United States Patent [19]

Bauer et al.

[11] 4,251,448
[45] Feb. 17, 1981

[54] MACROCYCLIC DIESTERS

[75] Inventors: Kurt Bauer; Alfred Körber; Karl-Heinz Bork, all of Holzminden, Fed. Rep. of Germany

[73] Assignee: Bayer Aktiengesellschaft, Leverkusen, Fed. Rep. of Germany

[21] Appl. No.: 71,350

[22] Filed: Aug. 30, 1979

[30] Foreign Application Priority Data

Jul. 24, 1979 [DE] Fed. Rep. of Germany ....... 2929864

[51] Int. Cl.³ .............................................. C07D 321/00
[52] U.S. Cl. ............................. 260/340.2; 252/522 R
[58] Field of Search ....................................... 260/340.2

[56] References Cited

U.S. PATENT DOCUMENTS 4,165,321  8/1979  Harris et al. ...................... 260/340.2

FOREIGN PATENT DOCUMENTS 223064  11/1942  Switzerland ........................... 260/340.2

Primary Examiner—Norma S. Milestone
Attorney, Agent, or Firm—Sprung, Felfe, Horn, Lynch & Kramer

[57] ABSTRACT

The invention concerns new macrocyclic diesters of the general formula:

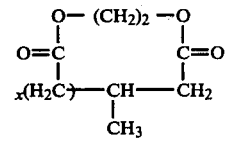

wherein x is an integer from 8 to 11, which are valuable odorants and a process for their preparation.

1 Claim, No Drawings

MACROCYCLIC DIESTERS

The invention relates to macrocyclic diesters of the formula

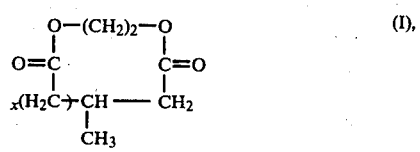

in which x represents an integer from 8 to 11.

The invention further relates to a process for the preparation of the diesters of formula (I). The process is characterised in that a compound of the general formula

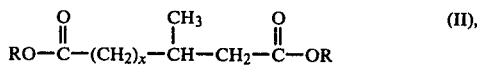

in which
R represents a hydrogen atom or a $C_1$-$C_4$-alkyl radical and
x represents an integer from 8 to 11, is reacted with ethylene glycol to form a polyester which is then depolymerised.

In addition the invention relates to the use of the macrocyclic diesters of formula (I) as odorants.

The preparation of the polyester can be conducted by reacting compounds of the general formula (II), in which R represents a $C_1$-$C_4$-alkyl group, preferably a methyl or ethyl group, with ethylene glycol in the presence of acids or bases.

Suitable acids are strong acids, such as sulphuric acid, anhydrous hydrogen chloride, toluene sulphonic acid or strongly acid cation exchangers. Possible bases are alkali hydroxides and alkali alcoholates such as sodium hydroxide, potassium hydroxide, lithium hydroxide, sodium methylate, sodium ethylate or preferably metallic sodium. Acids and bases are used in quantities conventionally used for reesterification catalysts.

The preparation of the polyester can also be conducted by esterification of the diacids of the general formula (II) with ethylene glycol in the presence of one of the above-mentioned strong acids. In this the alcohol is preferably used in excess and the reaction water which forms is removed from the reaction mixture with an entrainer such as chloroform or carbon tetrachloride.

The preparation of the polyester is however preferably conducted by esterification of the diacids of formula (II) with ethylene glycol without a catalyst and without an entrainer at temperatures of 120° to 200° C., preferably 160° to 180° C.

The polyester is thermally depolymerised, e.g. by heating to 250° to 300° C. The depolymerisation may optionally be conducted in the presence of conventional depolymerisation catalysts, such as magnesium chloride, magnesium oxide or lead oxide.

The compounds of the general formula (II) may be prepared in the following way: suberic acid, azelaic acid, sebacic acid or nonane dicarboxylic acid are converted into their half-ester chlorides according to known methods. These half-ester chlorides are reacted with dimethylacrylic acid ethyl ester in the presence of a Friedel Craft catalyst to form 3-methyl-5-oxo-diacid diethyl esters unsaturated in one position. These esters are converted with hydrazine into the diacids of the general formula (II) by means of hydrogenation in the presence of Raney nickel and subsequent Wolff Kishner reduction using hydrazine. The diacids obtained in this way may be converted into the diesters of formula (II) according to known esterification methods.

The macrocyclic diesters according to the invention are valuable odorants. Compared with the known brassylic acid ethylene esters they surprisingly have the advantage that they exhibit, in addition to a musk note, marked erogenous accents which remind one of costus root oil. They can, inter alia, therefore be used as a starting basis for new, erogenous, long-lasting fragrance notes or, in combination with other musk compounds, to intensify the latter or to give them a more natural character.

The compounds according to the invention are used in mixtures with other odorants in odorant compositions, e.g. in quantities of 0.01 to 25 percent by weight, related to the total weight.

The field of application of the compounds according to the invention is extraordinarily wide, owing to their harmonious type of odour and their advantageous properties for commercial application, e.g. their stability in aggressive media. They are suitable for use in perfume compositions for the most varied finished products, e.g. for high-quality cosmetics, for fine perfumery articles such as extraits, soaps, deodorant sprays, shampoos, foam baths and for detergents.

EXAMPLE 1

366 g (1.5 mols) 3-methyl-dodecanedioic acid are heated, whilst stirring, to 170° C. with 186 g (3 mols) ethylene glycol. During this process 20 g (1.1 mol) water are separated off. The polyester produced is freed in vacuo (2.7 mbars) from the remaining water and the excess ethylene glycol and subsequently mixed with 7.5 g magnesium oxide. This mixture is then introduced dropwise into a distillation apparatus, the flask of which is heated to 290° C. and kept under a vacuum of 0.9 to 1.5 mbars. At 127° to 135° C./1.2 mbar, 324 g of crude product are distilled off. From this, by means of fine distillation, 311 g 7-methyl-1,4-dioxa-cyclohexadecane-5,16-dione having a boiling point of 125° to 128° C./0.4 mbar are obtained, corresponding to a yield of 76.8% of theory, based on the diacid used.

The 3-methyl-dodecane dioic acid used as starting material is prepared according to the following method: 499.2 g (2.4 mols) suberic acid ethyl ester chloride and 307 g (2.4 mols) dimethylacrylic acid ethyl ester are simultaneously metered, over a period of 7 hours, into a suspension of 957.6 g (7.3 mols) aluminium chloride in 750 ml methylene chloride, the temperature being kept at 20° to 27° C. by means of cooling. When the addition has ended the reaction mixture is first of all heated for 3 hours to reflux temperature and is then hydrolysed with water/ice. The aqueous phase is extracted twice with methylene chloride. The combined organic phases are washed until neutral and the solvent is drawn off. 748 g crude 3-methyl-5-oxo-2(3)-dodecenedioic acid diethyl ester are obtained, which are introduced, without further purification, together with 295.1 g (5.27 mols) potassium hydroxide, 1944 ml ethanol and 1171 ml water, into an autoclave and hydrogenated under the addition of 100 g Raney nickel at 40° C. and 40.5 bar of hydrogen pressure. The adsorption of hydrogen is complete after 3.5 hours. After filtering off the catalyst the reaction solution is acidified with concentrated hydrochloric acid. First of all the majority of the ethanol is separated from the reaction solution in a thin-film evaporator. The residue is taken up in ether and washed until neutral. After the solvent has been drawn off 588 g crude 3-methyl-5-oxo-dodecanedioic acid remain.

The 588 g crude 3-methyl-5-oxo-dodecanedioic acid are heated, without further purification, for 2 hours to reflux temperature, together with 638.4 g (11.4 mols) potassium hydroxide, 2.41 diethylene glycol and 427 g (6.84 mols) 80% strength hydrazine hydrate. Then water and excess hydrazine are distilled off. The reaction temperature is kept at 190° to 200° C. until nitrogen evolution ceases. After cooling the reaction product is poured on to ice, is acidified with hydrochloric acid and extracted with ethyl acetate. After drawing off the solvent 366 g 3-methyl-dodecanedioic acid (m.p. 81°–82° C.) remain, corresponding to a yield of 62.5% of theory, based on the suberic acid half-ester chloride.

EXAMPLE 2

198 g (0.77 mols) 3-methyl-tridecanedioic acid are condensed, under the conditions described in Example 1 for the esterification of 3-methyl-dodecanedioic acid, together with 95 g (1.54 mols) ethylene glycol into the polyester. The polyester is then depolymerised, also under the conditions described in Example 1, in the presence of 4 g magnesium oxide. 170.6 g crude product and, after fine distillation, 160.3 g 7-methyl-1,4-dioxa-cycloheptadecane-5,17-dione with a boiling point of 140° C./0.53 mbars, are obtained, corresponding to a yield of 73.7% of theory, based on the diacid used.

The starting material 3-methyl-tridecanedioic acid (m.p. 68.5°–69.5° C.) is prepared, under the conditions described in Example 1 for the preparation of 3-methyl-dodecanedioic acid, from azelaic acid ethyl ester chloride and dimethylacrylic acid ethyl ester.

EXAMPLE 3

101 g (0.31 mols) 3-methyl-tetradecanedioic acid diethyl ester and 39 g (0.64 mol) ethylene glycol are heated to 110° C. After adding 0.5 g sodium the temperature is increased to 180° C. Within 2 hours 23.4 g ethanol are distilled off. By applying a vacuum any remaining ethanol and excess ethylene glycol are distilled off. The residue is taken up in chloroform and acidified with hydrochloric acid. The organic phase is washed until neutral and the solvent is drawn off. 87.7 g crude polyester are obtained which are mixed, without being further purified, with 1.7 g magnesium oxide and depolymerised as described in Example 1. At 140° to 160° C./1.3 mbar a crude product is obtained which, after fine distillation, yields 74 g 7-methyl-1,4-dioxy-cyclooctadecane-5,18-dione with a boiling point of 143° C./0.4 mbar, corresponding to a yield of 79% of theory, based on the diacid diethyl ester used.

The 3-methyl-tetradecanedioic acid diethyl ester used as starting material is prepared in the following way:

538 g (1.98 mols) 3-methyl-tetradecanedioic acid of a melting point of 75° C. are obtained by condensation, hydrogenation and Wolff Kishner reduction from 782 g (3.15 mols) sebacic acid ethyl ester chloride and 403 g (3.15 mols) dimethylacrylic acid ethyl ester according to the method described in Example 1 for the preparation of 3-methyldodecanedioic acid.

These 538 g (1.98 mols) 3-methyl-tetradecanedioic acid are heated to reflux temperature for 4 hours with 631 ml ethanol and 74.2 g concentrated sulphuric acid. Then excess ethanol is distilled off, the residue is added to water and extracted with toluene. Following fractionated distillation 616 g 3-methyl-tetradecanedioic acid ethyl ester are obtained having a boiling point of 175° to 185° C./0.8 mbar, corresponding to a yield of 59.6% of theory, based on the sebacic acid ethyl ester chloride used.

EXAMPLE 4

A Chypre composition is prepared by mixing the following components:

| | |
|---:|:---|
| 150 | bergamot oil/Reggio |
| 30 | lemon oil/Italian |
| 50 | linalool |
| 50 | benzyl acetate |
| 30 | methyldihydrojasmonate |
| 30 | jasmin absolue/Moroccan |
| 3 | dihydrojasmone |
| 100 | α-hexyl cinnamaldehyde |
| 38 | phenyl-ethyl alcohol |
| 30 | citronellol |
| 20 | eugenol |
| 1 | cumin oil |
| 10 | allyl ionone |
| 5 | undecalactone |
| 80 | γ-Iraldeine |
| 50 | vetiveryl acetate |
| 20 | sandalwood oil/East Indian |
| 30 | patchouli oil |
| 50 | oak moss absolue/Yugoslavian |
| 3 | vanillin |
| 780 | parts by weight |

By adding 15 parts by weight of 7-methyl-1,4-dioxa-cycloheptadecane-5,17-dione the base already assumes more radiance in its initial odour and a greater impact. In its after-odour the base is enriched by an interesting erogenous note, which does not give an imposing effect but rather gives the composition a soft, feminine note.

Similar results are obtained by the addition of 10 parts by weight of 7-methyl-1,4-dioxa-cyclohexadecane-5,16-dione or 8 parts by weight of 7-methyl-1,4-dioxacyclooctadecane-5,18-dione.

What is claimed is:

1. Macrocyclic diesters of the general formula:

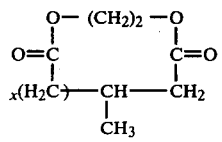

wherein x is an integer from 8 to 11.

* * * * *

UNITED STATES PATENT AND TRADEMARK OFFICE
CERTIFICATE OF CORRECTION

PATENT NO. : 4,251,448

DATED : Feb. 17, 1981

INVENTOR(S) : Kurt Bauer et al

It is certified that error appears in the above—identified patent and that said Letters Patent is hereby corrected as shown below:

Title Page, "Bayer Aktiengesellschaft, Leverkusen, Germany"
Assignee should be "Haarman & Reimer, Holzminden, Germany".

Signed and Sealed this

Thirteenth Day of October 1981

[SEAL]

*Attest:*

GERALD J. MOSSINGHOFF

*Attesting Officer*     *Commissioner of Patents and Trademarks*